United States Patent
Kamata et al.

(12)

(10) Patent No.: US 6,565,507 B2
(45) Date of Patent: May 20, 2003

(54) FLEXIBLE TUBE, AND METHOD FOR MANUFACTURING SAME

(75) Inventors: Kouichi Kamata, Okegawa (JP); Haruo Akiba, Koga (JP); Masanori Kimura, Oyama (JP); Kouichi Muraki, Sowa-machi (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 33 days.

(21) Appl. No.: 09/950,653

(22) Filed: Sep. 13, 2001

(65) Prior Publication Data

US 2002/0032370 A1 Mar. 14, 2002

(30) Foreign Application Priority Data

Sep. 13, 2000 (JP) ......................................... 2000-278310

(51) Int. Cl.[7] .................................................. A61B 1/00
(52) U.S. Cl. ........................ 600/153; 600/139; 600/140
(58) Field of Search ................................. 600/153, 139, 600/140, 144; 604/523, 524; 428/34.1, 34.6, 34.7, 35.7, 35.9, 36.9, 36.91

(56) References Cited

U.S. PATENT DOCUMENTS

| | | | |
|---|---|---|---|
| 3,799,152 A | * | 3/1974 | Kim ........................... 600/139 |
| 5,176,659 A | * | 1/1993 | Mancini ..................... 604/523 |
| 5,718,973 A | * | 2/1998 | Lewis et al. ............... 623/1.32 |
| 5,738,630 A | * | 4/1998 | Suzuki et al. .............. 600/121 |
| 5,789,047 A | * | 8/1998 | Sasaki et al. ............. 428/36.91 |

* cited by examiner

Primary Examiner—Linda C. M. Dvorak
Assistant Examiner—Kenneth G Schopfer
(74) Attorney, Agent, or Firm—Oblon, Spivak, McClelland, Maier & Neustadt, P.C.

(57) ABSTRACT

A flexible tube having a laminated multi-layer structure including an outer layer composed of a main tube body layer formed of thermoplastic synthetic resin in a predetermined thickness and a reinforcing layer provided on the inner side of the main tube body layer, and an inner layer formed of a thin film sheet of air tight and low friction material. The inner layer is formed by rolling an elongated strip of a thin film sheet into a tubular form such that opposite lateral sides of the thin film sheet are overlapped one on the other to provide a thick wall portion extending longitudinally of and at one angular position of the inner layer.

8 Claims, 10 Drawing Sheets

FLEXIBLE TUBE, AND METHOD FOR MANUFACTURING SAME

BACKGROUND OF THE INVENTION

1. Field of the Art

This invention relates to a flexible tube which is particularly useful, for example, as a biopsy channel or guide tube to be incorporated into an endoscopic insertion instrument or as a catheter or the like, and a method for manufacturing such guide tubes.

2. Prior Art

Generally, endoscopes which are in use in medical fields are constituted by a manipulating head assembly to be gripped by an operator and an insertion instrument which is extended forward from the manipulating head assembly for insertion into a patient's body cavity. By way of properties, an endoscopic insertion instrument can be divided into three sections, i.e., a rigid tip end section which is provided at a fore distal end of the insertion instrument, an angle section which is connected to a proximal end of the rigid tip end section, and an elongated flexible body section which is connected between a proximal end of the angle section and the manipulating head assembly. Endoscopic observation means are provided on the rigid distal end section for observation of intracavitary portions, including an illumination window or windows having a light emitting end of a light guide fitted therein for projecting illumination light, and an observation window having an optical lens system fitted therein for picking up optical images of intracavitary portions. Further, an exit hole of a biopsy channel is opened in the rigid tip end section for projecting forceps or other biopsy or surgical instrument into a body cavity therethrough.

The angle section is a part which can be flexibly bent into an angular form by remote control from the manipulating head assembly. The flexible body section has a flexible structure which is bendable in arbitrary directions along a path of insertion into a body cavity. Various component parts which are fitted in or threaded through the flexible body section should also be flexible in bending directions of the insertion instrument. In this connection, the biopsy channel is extended coextensively through the insertion instrument, more specifically, from a fore distal end of the insertion instrument up to an entrance hole or an entrance way which is provided on the manipulating head assembly. Forceps or other instruments which are introduced into the biopsy channel through the entrance hole are projected into a body cavity through the exit hole which is formed in the rigid tip end section of the insertion instrument to make a necessary treatment. Therefore, the biopsy channel is required to be flexible in bending directions and is usually constituted by a flexible tube. The biopsy channel which is fundamentally provided for insertion of biopsy instruments is also used as a suction passage at the time of sucking out body fluids or the like. In addition to a biopsy channel, a flexible tube of similar nature is also fitted in the endoscopic insertion instrument to serve as an air/water feed tube for the purpose of washing the observation window.

In addition to the afore-mentioned flexibility, the flexible tubes which are used in medical treatments as endoscopic biopsy channels or for other purposes are required to have satisfactory properties in shape retainability including anti-crushing strength, anti-kinking strength, anti-rupturing strength, air tightness, water tightness, resistance to chemicals, feasibility of disinfection by washing, biotic suitability or safety etc. Especially, a flexible tube to be use as an endoscopic biopsy channel should be formed of a material which is slippery and of low frictional coefficient in order to ensure smooth insertion of various instruments. The inside diameter of an endoscopic biopsy channel is determined depending upon outside diameters of endoscopically inserting instruments, and is normally in the range of 1 mm to 5 mm. Besides, in order to make the outside diameter as small as possible, a flexible tube for a biopsy channel is usually arranged to have a minimum necessary wall thickness.

For instance, disclosed in Japanese Patent Publication H7-45219 is a flexible tube which was developed to meet the above-mentioned requirements in properties. This known flexible tube is of a laminated structure consisting of an inner layer and an outer layer. The inner layer is formed by extruding a crystalline polymer resin consisting of a fluorine resin or the like into a tubular form. This inner layer is particularly so arranged as to have properties which are required of the inner layer of the biopsy channel, namely, to have suitable properties in slipperiness, low friction coefficient, resistance to chemicals, feasibility of disinfection by washing and biotic safety, in addition to air- and water-tightness. However, the crystalline polymer resin itself is inferior flexibility. Therefore, the thickness of the inner layer is reduced as much as possible for the purpose of imparting flexibility thereto, at the sacrifice of strength. For these reasons, the outer layer needs to be imparted with necessary properties in strength, including shape retainability and anti-rupturing strength, in addition to flexibility. Therefore, the outer layer is formed of a thermoplastic resin, desirably urethane resin. In order to enhance the strength of the outer layer, a reinforcing layer is embedded in urethane resin or a reinforcing layer is sandwiched between urethane resin layers. Mesh-like knit fabric of metal fiber is used as a reinforcing layer for the purpose of ensuring flexibility in bending directions.

The arrangement of above-described prior art flexible tube can be advantageously used as an endoscopic biopsy channel. However, this prior art flexible tube still has a number of problems. One problem relates to the wall thickness of the flexible tube. The use of the outer layer, having a reinforcing layer sandwiched between urethane resin layers, makes reductions in wall thickness very difficult. In addition, reductions in wall thickness are also difficult with regard to the inner layer which is formed by extrusion molding. Thus, the prior art flexible tube has limits in reducing the wall thickness of the flexible tube as a whole.

In the case of an endoscope which is designed for medical use, it is desirable for the insertion instrument to be as thin as possible from the standpoint of reducing pains on the part of patients and facilitating passage through a narrow duct. Recently, the insertion instrument itself of an endoscope as well as internally fitted members of the insertion instrument are reduced in diameter almost to ultimate limits. Nevertheless, regarding the biopsy channel which occupies a relatively large space within the endoscopic insertion instrument, use of a flexible tube which is thinned down in wall thickness and in diameter and yet can meet the above-mentioned requirements in properties can contribute significantly in further reducing diameters of endoscopic insertion instruments.

On the other hand, as for a flexible tube which is intended for use as an endoscopic biopsy channel or for other medical use, Laid-Open Japanese Utility Model H4-47402 discloses a flexible tube construction having an inner layer or inner tube of fluororesin wrapped in a helical metal wire winding, and an outer layer of urethane resin which is laminated around the inner layer. In the case of this prior art flexible tube having a reinforcing layer formed directly around the outer periphery of the inner layer, the outer layer can be constituted by a single urethane resin layer. Therefore, since the properties such as anti-kinking strength, shape retainability and anti-rupturing strength can be covered by the outer layer, it becomes possible to reduce the wall thickness almost to an ultimate limit. However, the use of a helical metal wire winding as a reinforcing layer is insufficient in guaranteeing required shape retainability and strength of the biopsy channel particularly when a load is exerted in a twisting direction.

Further, the above-mentioned properties such as air tightness, water tightness, slipperiness, low friction coefficient, resistance to chemicals, feasibility of disinfection by washing and biotic safety are properties which are required of interior and exterior surfaces of a flexible tube, and do not necessarily have direct relation with the wall thickness. Therefore, it is desirable for the inner layer to be formed as thin as possible. However, the inner layer of the flexible tube in the above-mentioned Laid-Open Japanese Utility Model H4-47402 is formed by extrusion molding.

Further, disclosed in Laid-Open Japanese Patent Specification H5-95892 is a flexible tube having a tubular inner layer which is formed of a tape with necessary properties. From the standpoint of reducing the wall thickness, it is easier to form a tubular body by the use of a tape than forming a tubular layer by extrusion molding. The tube which is disclosed in Laid-Open Japanese Patent Specification H5-95892 employs a tape of a non-calcined tetrafluoroethylene resin in forming a tubular body. More specifically, an inner layer is formed by helically winding a tape material around a core wire in such a way that adjacent helices are overlapped one on the other to a predetermined extent, and then a reinforcing layer is formed by winding a stainless steel filament around the outer periphery of the inner layer, followed by sintering in a heating furnace to connect tightly to each other the overlapped portions of adjacent helices as well as the tape and the steel wire filament. Further, around the inner and reinforcing layers thus formed, an outer layer is formed by winding a non-calcined tetrafluoroethylene resin tape, and the resulting tube assembly is fired again in a heating furnace to connect the inner and outer layers integrally to each other.

In this connection, in forming a tubular inner layer by the use of a tape, it is important to over the adjacent helices to a predetermined extent in order to ensure air- and water-tightness which is essentially required of the inner layer. This however results in variations in thickness of the inner layer, which contains alternately a thick portion and a thin portion. Therefore, an instrument which has been inserted into a biopsy channel has to ride over the thick portions as it progresses toward an exit of the biopsy channel. For this reason, the flexible tube which is disclosed in Laid-Open Japanese Patent Specification H5-95892 is not necessarily suitable for use as a biopsy channel to be incorporated into an endoscopic insertion instrument, considering its non-smooth interior surface conditions.

Further, for the purpose of turning into a desired direction a rigid tip end section which is provided with illumination and observation windows along with an exit opening of a biopsy channel, an angle section is provided on the proximal side of the rigid tip end section. This angle section is flexibly bent into angular forms by remote control from the side of a manipulating head assembly of an endoscope. In this regard, in order to permit an operator to change the direction of observation view field, normally the angle section is arranged to be angularly flexible through 180 degrees or more. In some cases, there arises a necessity for inserting an instrument into a biopsy channel even when the angle section is in an angularly bent form. On such an occasion, the inserted instrument is forcibly pressed against inner surfaces of the angle section, on the outer side of the bend, as it progresses toward an exit at the distal end of the rigid tip end section.

As discussed above, in a case where the wall thickness of an inner layer of a flexible tube is reduced almost to an ultimate limit, it is very likely that repeated insertions of biopsy or surgical instruments can cause frictional wear or damages to certain localities of the inner layer and result in inward exposure of the outer layer through ruptured portions of the inner layer. This of course detrimentally affects the feasibility of disinfection by washing and resistance to chemicals on the interior side of the flexible tube. Therefore, in developing a flexible tube with interior surfaces of suitable properties for use as a biopsy channel on a medical endoscope, there have been limits to the reduction of wall thickness of an inner layer of the flexible tube, making it extremely difficult to reduce the diameter of the endoscopic biopsy channel.

SUMMARY OF THE INVENTION

In view of the foregoing situations, it is an object of the present invention to provide a flexible tube with an extremely thin inner layer which is almost free from frictional wear or damages by frictional contact, and a method for manufacturing such a flexible tube.

It is another object of the present invention to provide a flexible tube which can be reduced in diameter, without sacrificing properties which are required for application to medical diagnostic or therapeutic instruments.

It is still another object of the present invention to provide a flexible tube of the sort as mentioned above, which can contribute to reduce the outside diameter of an endoscopic insertion instrument when applied as a biopsy channel of the insertion instrument.

In accordance with the present invention, in order to achieve the above-stated objectives, there is provided a flexible tube, which comprises: an outer layer including a main tube body layer formed of a thermoplastic synthetic resin in a predetermined thickness, and a reinforcing layer provided integrally on the inner side of the main tube body layer; and an inner layer formed of a thin film of air tight and low friction material provided on the inner side of the reinforcing layer; the inner layer being formed by rolling a thin film into a tubular form in such a way that opposite sides of the thin film are overlapped one on the other to a predetermined degree to form a thick wall portion of a predetermined width extending longitudinally of and at one angular position of the tubular inner layer.

The inner layer which is formed into a tubular shape contains a thick wall portion. However, except the thick wall portion extending in the axial or longitudinal direction, the inner layer contains no other thick wall portions which extend in other directions on the inner periphery of the inner layer. The inner layer is formed of a thin film substantially of uniform thickness, which is rolled on itself at least by one turn and such that one lateral side of the thin film is overlapped on the other lateral side to a predetermined degree to formed a thick wall portion of a predetermined width extending in the longitudinal direction of the inner layer.

The flexible tube according to the present invention can be advantageously used as a biopsy channel of an endoscopic insertion instrument.

Namely, according to the present invention, there is provided a flexible tube to be fitted in an insertion instrument of an endoscope to serve as a biopsy channel for insertion of biopsy or surgical therapeutic instruments, the flexible tube comprising: a laminated multi-layer structure including an outer layer including a main tube body layer formed of a thermoplastic synthetic resin in a predetermined thickness, and a reinforcing layer provided integrally on the inner side of the main tube body layer, and an inner layer formed of a thin film of air tight and low friction material provided on the inner side of the reinforcing layer; the inner layer being formed by rolling a thin film into a tubular form in such a way that opposite sides of the thin film are overlapped one on the other over a predetermined width to form a thick wall portion of a predetermined width extending in the longitudinal direction of the inner layer; and the thick wall portion being located in an angular position of the biopsy channel where the biopsy or surgical instrument are slid against an inner surface of the biopsy channel when an angle section of the endoscopic instrument is flexibly bent into an angular form.

In a case where the angle section of the endoscopic insertion instrument is flexibly bendable at least in two predetermined directions, preferably the inner layer is formed of a plural number of thin films to provide longitudinal thick wall portions of a predetermined width at such angular positions of the inner layer that each is located on the outer side of a bend when the angle section of the endoscopic insertion instrument is bent in either one of the two directions.

The inner layer is formed of a thin film sheet which possesses necessary properties for the inner surface of the flexible tube. In the case of an inner surface of a biopsy channel of an endoscopic insertion instrument, it is required to have satisfactory properties in air tightness, liquid tightness, slipperiness, resistance to chemicals, feasibility of disinfection by washing, biotic safety etc. In order to meet these requirements, the thin film sheet for the inner layer is preferred to be of either non-calcined tetrafluoroethylene resin or non-calcined hexafluoroethylene resin. On the other hand, the outer layer of the flexible tube is composed of the above-mentioned main tube body layer and reinforcing mesh layer and required to have sufficient strength in shape retainability and anti-rupturing strength. In this regard, preferably the main tube body layer is formed of at least one member selected from a group consisting of urethane resin, nylon and polyethylene, and the reinforcing layer is formed of metal netting in the form of knit fabric of metallic filaments.

Further, according to the present invention, there is also provided a method for manufacturing a flexible tube having a laminated multi-layer structure including an outer layer including a main tube body layer formed of a thermoplastic synthetic resin in a predetermined thickness, and a reinforcing layer provided integrally on the inner side of the main tube body layer, and an inner layer formed of a thin film of air tight and low friction material provided on the inner side of the reinforcing layer, the method comprising the steps of: forming the inner layer by wrapping an elongated strip of a thin film sheet around a core rod in such a way that opposite lateral sides of the thin film sheet are overlapped one on the other to a predetermined degree to provide a thick wall portion of a predetermined width extending longitudinally of and at one angular position of the inner layer; etching outer peripheral surfaces of the inner layer on the core rod; forming a reinforcing mesh layer on and around the inner layer by knitting metal filaments directly on and around etched outer surfaces of the inner layer; and forming the main tube body layer by laminating a thermoplastic resin on and around the reinforcing mesh layer.

The above and other objects, features and advantages of the present invention will become apparent from the following particular description of the invention, taken in conjunction with the accompanying drawing which show by way of example its preferred embodiments. Needless to say, the present invention should not be construed as being limited to particular embodiments shown.

DESCRIPTION OF PREFERRED EMBODIMENTS

Hereafter, the present invention is described more particularly by way of its preferred embodiments shown in the accompanying drawings. Firstly, reference is had to FIG. 1 which shows the general layout of a flexible tube which constitutes an endoscopic biopsy channel, and to FIG. 2 which shows the flexible tube in a transverse section.

Figure 1:
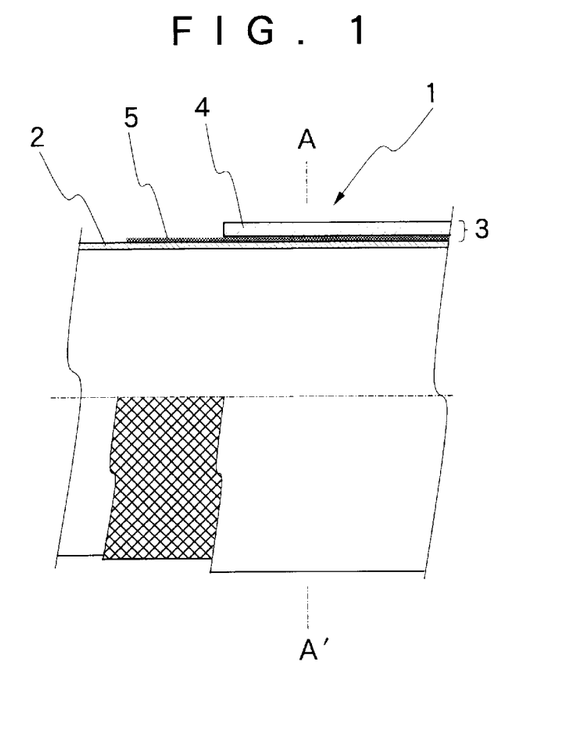
FIG. 1 is a schematic illustration of a flexible tube embodying the present invention.
Figure 2:
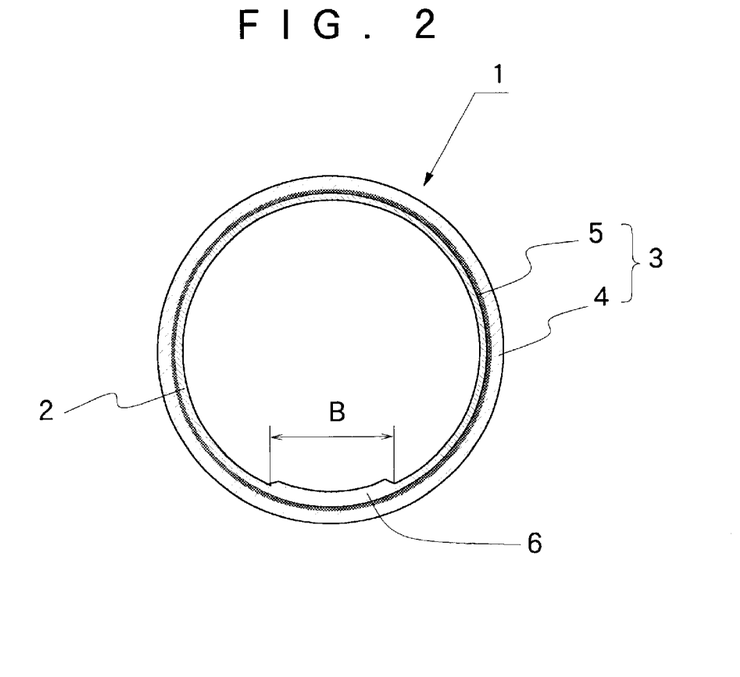
FIG. 2 is a schematic sectional view taken on line A-A' in FIG. 1.

As clear from these figures, a flexible tube 1 which constitutes a biopsy channel in an endoscopic insertion instrument is composed of an inner layer 2 and an outer layer 3. The inner layer 2 is formed of a thin film tube of air tight and low friction coefficient material, preferably of tetrafluoroethylene resin (PTFE) or non-calcined hexafluoroethylene resin. On the other hand, the outer layer 3 is formed of a main tube body layer 4 and a reinforcing layer 5 which consists of metal mesh or metal knit fabric. The mesh 5 is directly laminated on the inner layer 2, and is formed by knitting or weaving hard metal fiber having spring action, for example, like hard stainless steel fiber, amorphous metal fiber or tungsten fiber. As described hereinlater, the main tube body layer 4 consists of a urethane resin layer which is formed on the mesh layer 5 by extrusion molding.

The inner layer 2, which is formed of a fluorine-base resin, serves to impart slipperiness to the inner surface of the flexible tube 1. Accordingly, the inner layer 2 is in the form of a thin film having a thickness approximately in the range of 0.03 mm to 0.2 mm. Considering washability, the thin film of the inner layer 2 is preferred to be non-porous and to have extremely smooth surfaces of low friction coefficient. On the other hand, in order to guarantee shape retaining capacity even when the endoscopic insertion instrument is bent to a maximum degree, the mesh layer 5 which constitutes part of the outer layer 3 is constituted by a knitting of intertwined filaments of hard stainless steel, for example, of SUS 304 WPB and of approximately 0.1 mm in diameter. In some cases, the angle section is bent through approximately 180 degrees in a radius of curvature of about 15 mm. In order to ensure sufficient flexibility on such an occasion, the bias angle of the knitting which constitutes the mesh layer 5 is preferred to be approximately in the range between 70 degrees and 50 degrees. Further, the main tube body layer 4 should have a thickness which is sufficient for completely covering the mesh layer 5, and at the same time should be of a soft type, for example, 80 degrees polyurethane which will not resist or distort movements of the mesh layer 5 when stretched or contracted within the flexible tube 1 by flexure of the latter.

In this instance, the outer layer 3 which is composed of the main tube body layer 4 and the mesh layer 5 needs to be connected to the inner layer 2 as firmly as possible to prevent detachment or exfoliations which might occur in boundary regions when the flexible tube is repeatedly bent in arbitrary directions. In this regard, an adhesive can be used for bonding the outer and inner layers 3 and 2 to each other. However, from the standpoint of higher integration of the two layers, it is preferable to laminate the outer layer 3 on the inner layer 2 by the use of a molding means. In this regard, the fluorine resin inner layer 2 has extremely smooth surfaces, so that an outer layer which is formed simply by laminating urethane resin on the inner layer 2 can be incapable of forming strong bondage to the inner layer 2 and can be easily detached from the latter. In order to avoid this problem, an etching treatment is given to the outer peripheral surface of the tube before laminating the mesh layer 5 and the main tube body layer 4 successively thereon.

Described below is a method for fabricating the flexible tube 1.

Figure 3:
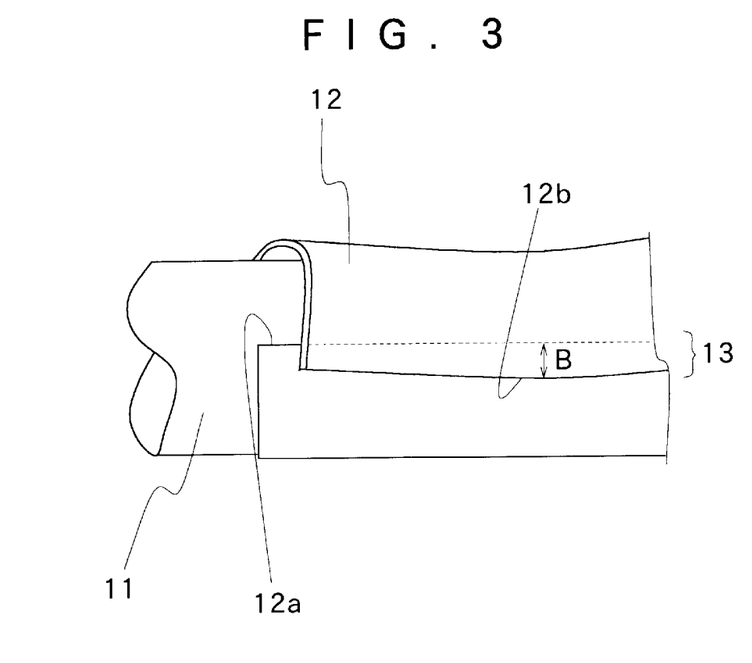
FIG. 3 is a fragmentary sectional view of an inner layer which is being formed by wrapping a thin film sheet around a core material.

In a first stage of a fabrication process, an inner layer 2 in the form of a thin film tube is formed in the manner as shown in FIG. 3. More specifically, a thin film sheet 12 is formed into a tubular shape by wrapping same around a core rod 11 of metal or other suitable material. Thus, the inside diameter of the flexible tube 1 is determined by the outside diameter of the core 11. The thin film sheet 12 is of a fluorine resin, for example, of a non-calcined tetrafluoroethylene resin (PTFE) and has a thickness in the range of from 0.03 mm to 0.2 mm. As clear from FIG. 2, the thin film sheet 12 is wrapped around the core rod 11 not just one round but wrapped in such a way that extra margins 12a and 12b at the opposite meeting ends of the thin film sheet 12 are overlapped one on the other over a predetermined width B. Therefore, the resulting thin film tube contains a double-thick overlapped portion 13 which extends longitudinally of the tube at one side thereof and in parallel relation with the axis of the core 11. The thin film sheet 12 which is in a non-calcined state at this stage is hardened by firing in a later stage.

Figure 4:
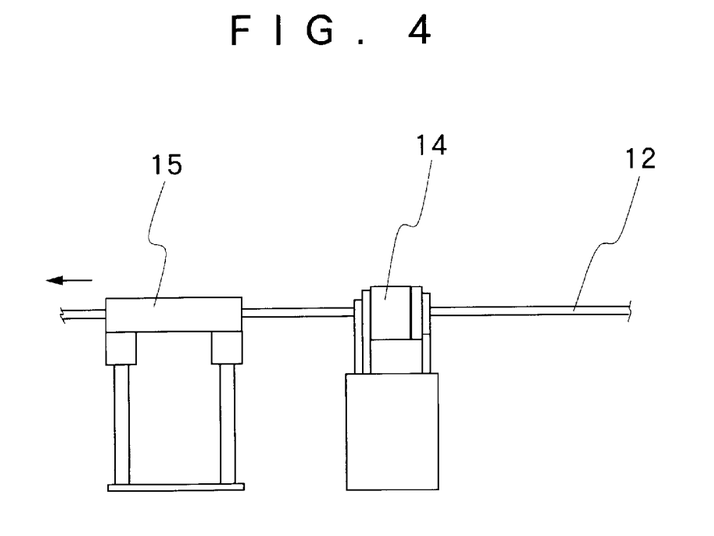
FIG. 4 is a schematic illustration explanatory of an inner layer forming operation.
Figure 5:
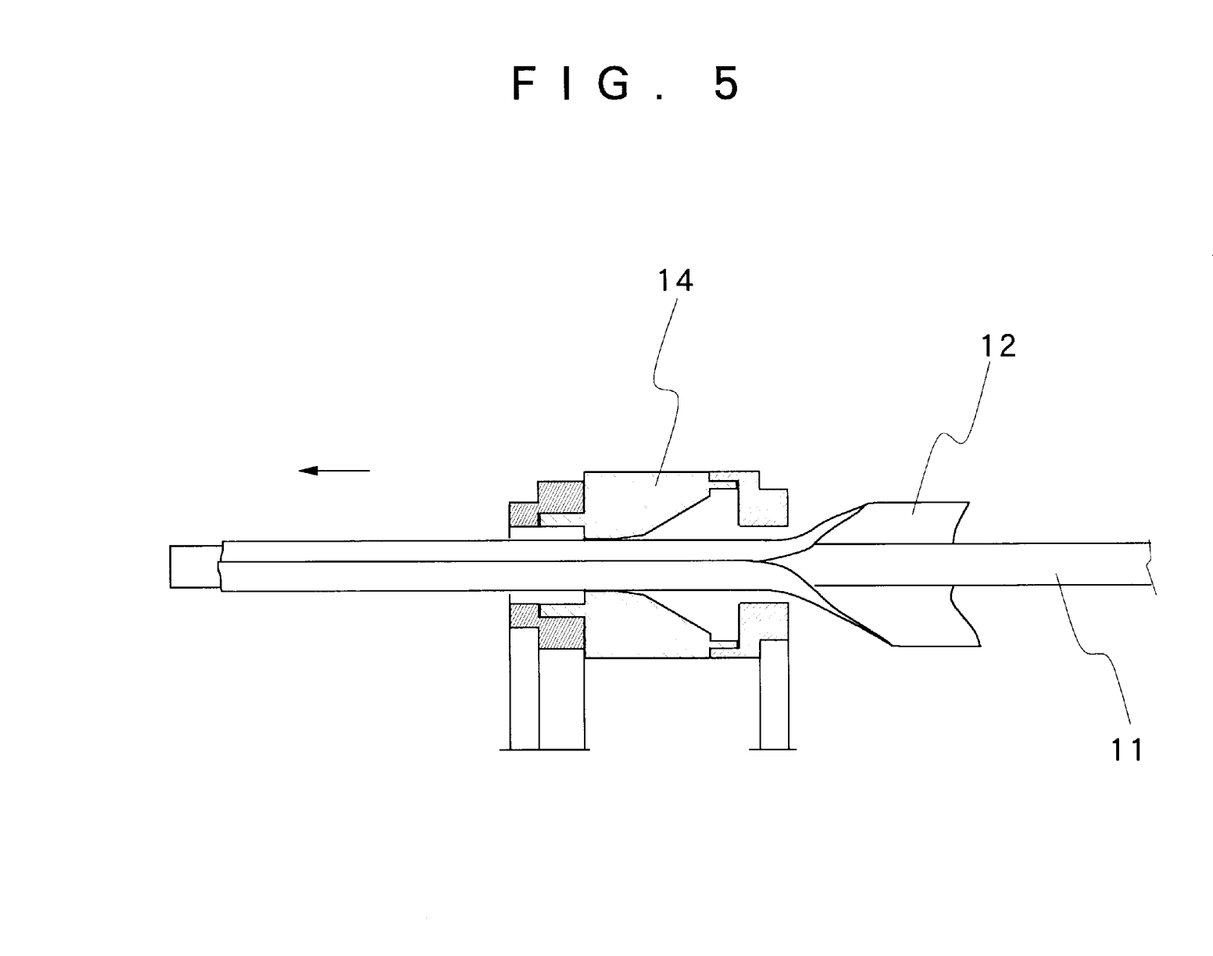
FIG. 5 is a schematic sectional view of a drawing die.

Shown in FIGS. 4 and 5 are a stage for forming the thin film sheet 12 into a cylindrical shape and a succeeding firing stage. In these figures, indicated at 14 is a drawing die and at 15 a firing furnace. The core rod 11 is in the form of a lengthy round rod, and the thin film sheet 12 is in the form of an elongated strip having a width which corresponds to the circumferential length of the core rod 11 plus the widths of the overlapping margins 12a and 12b. While the core rod 11 is fed in a forward direction as indicated by an arrow in FIG. 5, the thin film sheet 12 is wrapped around the circumference of the core rod 11 within the drawing die 14. Past the drawing die 14, the rolled thin film 12 on the core rod 11 is calcined in the firing furnace 15 approximately at 400° C. for 10 to 60 seconds. The overlapped portions intimately adhered to each other, and at the same time the rolled thin film sheet 12 as a whole is thermally hardened by calcination to form the tubular inner layer 2. Accordingly, the inner layer 2 of PTFE comes to have flexibility in bending directions because it is extremely thin. The thin film sheet 12 of the inner layer 2 is non-porous and, because of the overlapped portion, the inner layer 2 can guarantee extremely air- and water-tightness. The overlapped portion forms a thick wall portion 6 of a predetermined width which extends longitudinally of the tubular inner layer 2. After firing and hardening, the thick wall portion 6 is approximately doubled in thickness, more specifically, is 1.7 times as thick as remainder portions of the inner layer 2.

Outer surfaces of the tubular inner layer 2, thus obtained, are then etched by a chemical etching treatment. For a chemical etching treatment, the inner layer 2 is immersed in an etching solution dissolving a complex of sodium and ammonia or an etching solution dissolving a complex of sodium and naphthalene in tetrahydrafuran. In the time of this chemical etching, the inner layer 2 is still fitted on the core 11.

By the chemical etching treatment, outer surfaces of the inner layer are roughened to increase the strength of bond to other synthetic resin material of the fluorine resin which normally has extremely weak bonding strength to other synthetic resin material. For example, due to inferior bonding strength of fluorine resin, it is difficult to laminate a thermoplastic resin directly on the inner layer 2. However, an etching treatment solves this problem and can preclude possibilities of detachment or exfoliation of a thermoplastic resin layer which is laminated on the inner layer 2. The time duration of immersion in the etching solution is suitably in the range of from 1 to 60 seconds. In this regard, it is to be understood that the etching treatment for roughening the outer surfaces of the inner layer 2 is not limited to chemical etching treatments but can be a mechanical abrasive etching treatment.

Figure 6:
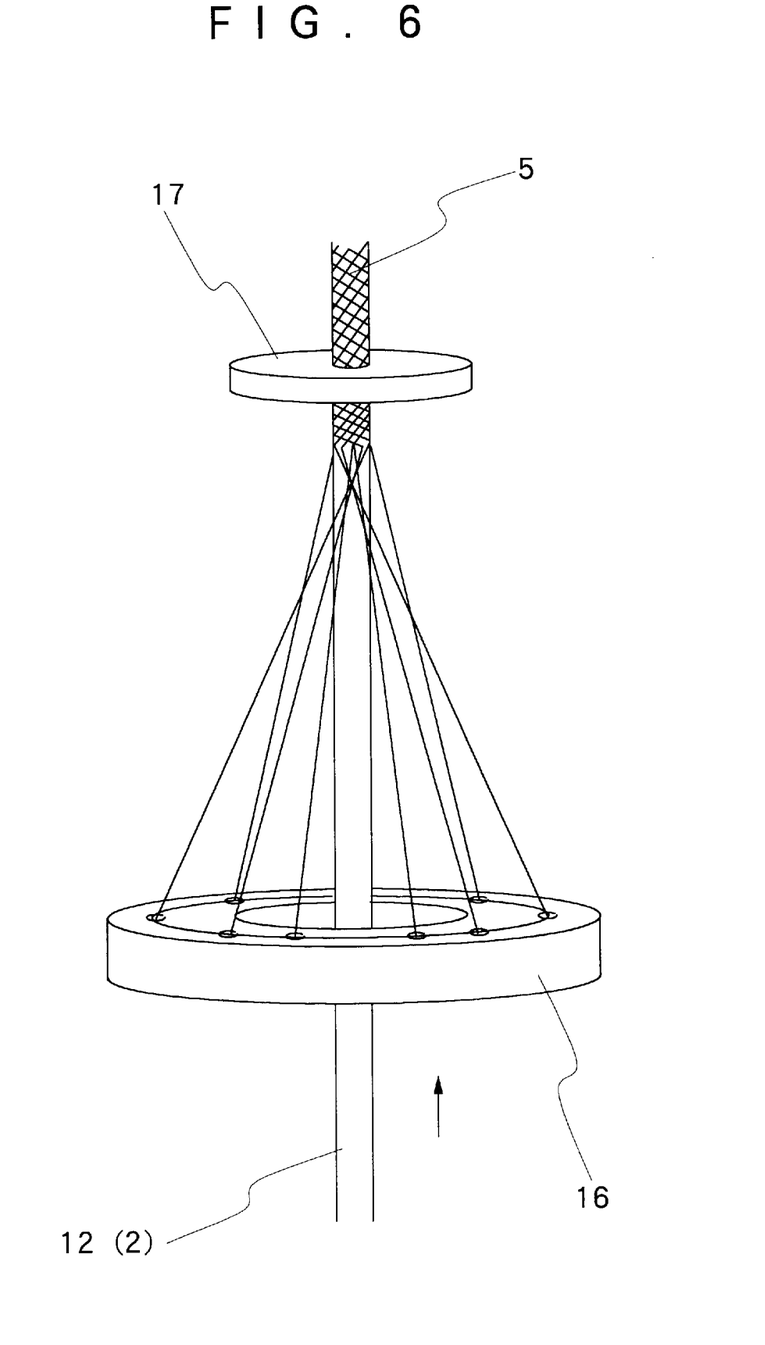
FIG. 6 is a schematic illustration explanatory of a netting operation.
Figure 7:
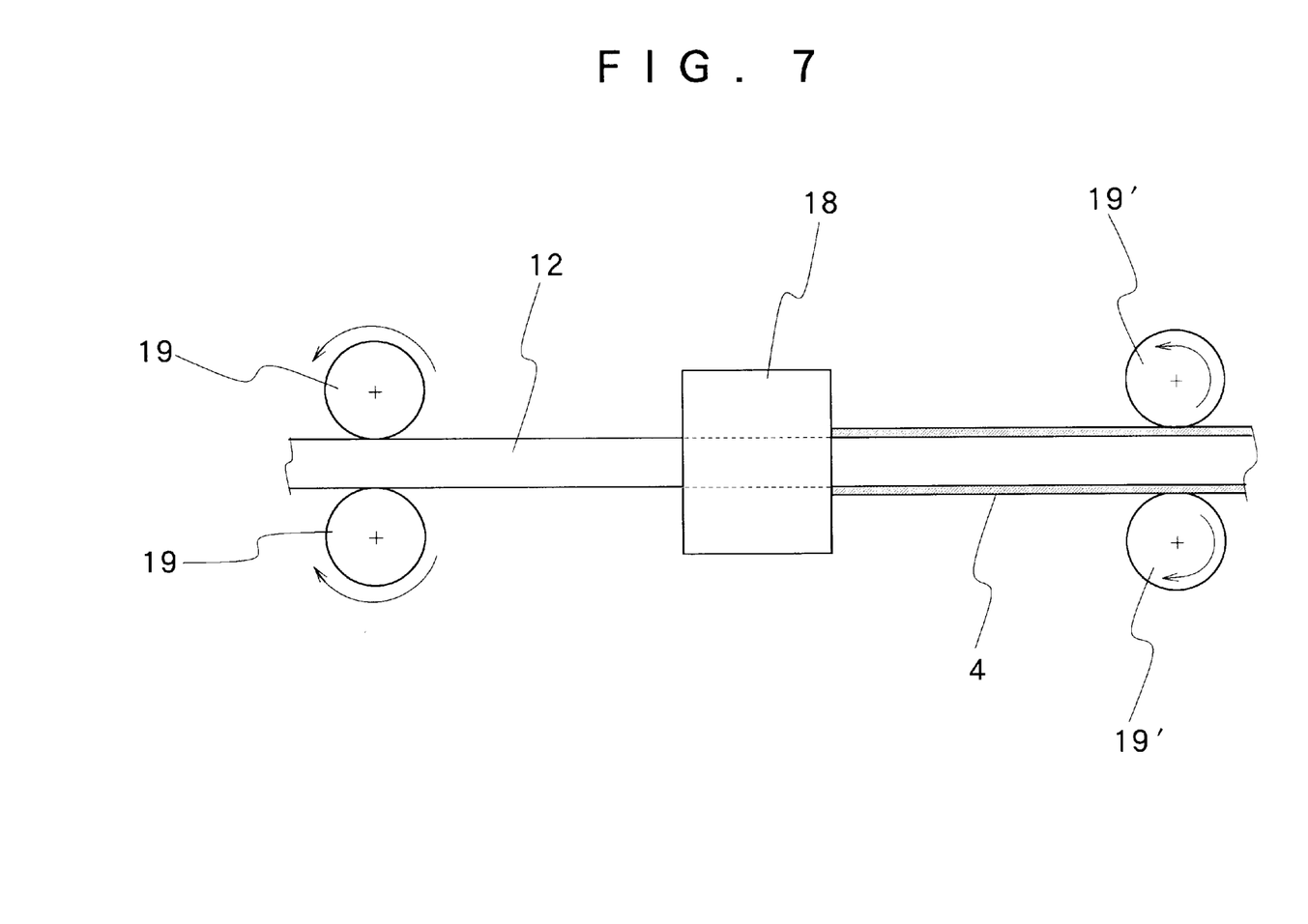
FIG. 7 is a schematic illustration explanatory of an operation of forming a main tube body layer.

Then, a mesh layer 5 of knit metal fiber is formed as a reinforcing layer on and around the etched outer surfaces of the inner layer 2, which is still on the core 11. More specifically, in this particular embodiment, the mesh layer 5 is knit on and around the inner layer 2 by the use a netting frame 16 and a positioning ring 17 as shown in FIG. 6. While the inner layer 2 is being fed in the direction indicated by an arrow, a number of groups of metal filaments are intertwined with each other in shifted positions. Direct knitting of the mesh layer 5 on the inner layer 2 is preferable from the stand point of shape retainability. After forming the mesh layer 5 on and around the inner layer 2, the main tube body layer 4 is laminated on in such a way as to completely cover the mesh layer 5. Thus, the outer layer 3 which is composed of the mesh layer 5 and the main tube body layer 4 is formed integrally around the inner layer 2. In this regard, the main tube body layer 4 can be laminated on the mesh layer 2 which is directly knit on the inner layer 2, for example, by the use of an extruder or extrusion molding machine 18 as shown in FIG. 7. In this case, feed rollers 19 and 19' are provided on the upstream and downstream sides of the extruder 18 to feed the assembled tube in the direction indicated by an arrow in FIG. 7.

Further, if necessary, compressive force may be applied on the main tube layer 4 to bond the main tube body layer 4 more intimately to the mesh layer 5 and inner layer 2. The flexible tube 1 of the ultimate product is thus formed on the core rod 11. After extraction of the core rod 11, the flexible tube 11 is cut into a unit length, for example, into a length suitable for use as a biopsy channel of an endoscope.

The inner PTFE layer 2 of the flexible tube 11 has excellent properties in slipperiness, low friction coefficient, resistance to chemicals, disinfection by washing, biotic safety etc. In addition, the inner layer 2, formed of a non-porous thin film having longitudinal side portions intimately overlapped and closed one on the other, also has excellent properties in air- and water-tightness. On the other hand, the outer layer 3, which is composed of the main tube body layer 4 of a urethane resin and the mesh layer 5, is imparted with satisfactory properties in strength such as, for example, in shape retainability and anti-rupturing strength. Furthermore, all of the component parts of the flexible tube 1, i.e., the inner layer 2, mesh layer 5 and main tube body layer 4, have sufficient flexibility at least in bending directions. The existence of the thick wall portion 6 in the inner layer 2 does not give rise to any problem in this regard because it is formed of an extremely thin film and as thin as 0.3 mm to 0.2 mm even in that portion. Moreover, the outer surface of the inner layer 2, roughened by an etching treatment, is capable of forming a sufficiently strong bond to the outer layer 3 for preventing exfoliation of tube layers. Furthermore, the flexible tube construction, having the inner layer 2 of an extremely thin film, the mesh layer 5 directly knit on and around the inner layer 2 and the main tube body layer 4 laminated around the mesh layer 5, can contribute to reduce the thickness of the flexible tube 1 as a whole to a considerable degree.

The flexible tube 1, with the above-described properties, can be widely applied to medical endoscopes or to serve other purposes in medial fields. However, it can be most suitably applied as an endoscopic biopsy channel.

Figure 8:
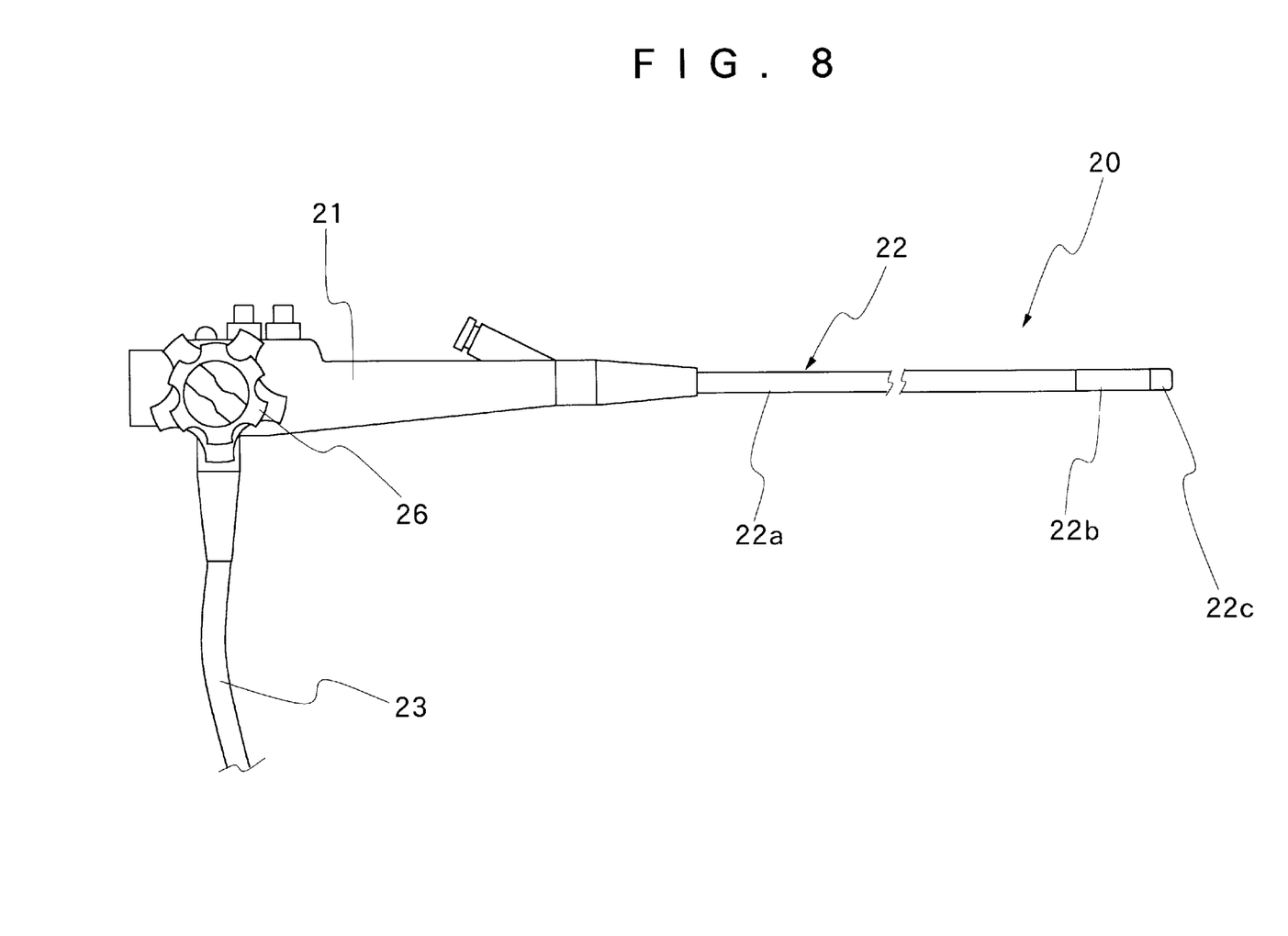
FIG. 8 is a schematic outer view of an endoscope incorporating a flexible tube according to the present invention as a biopsy channel.
Figure 9:
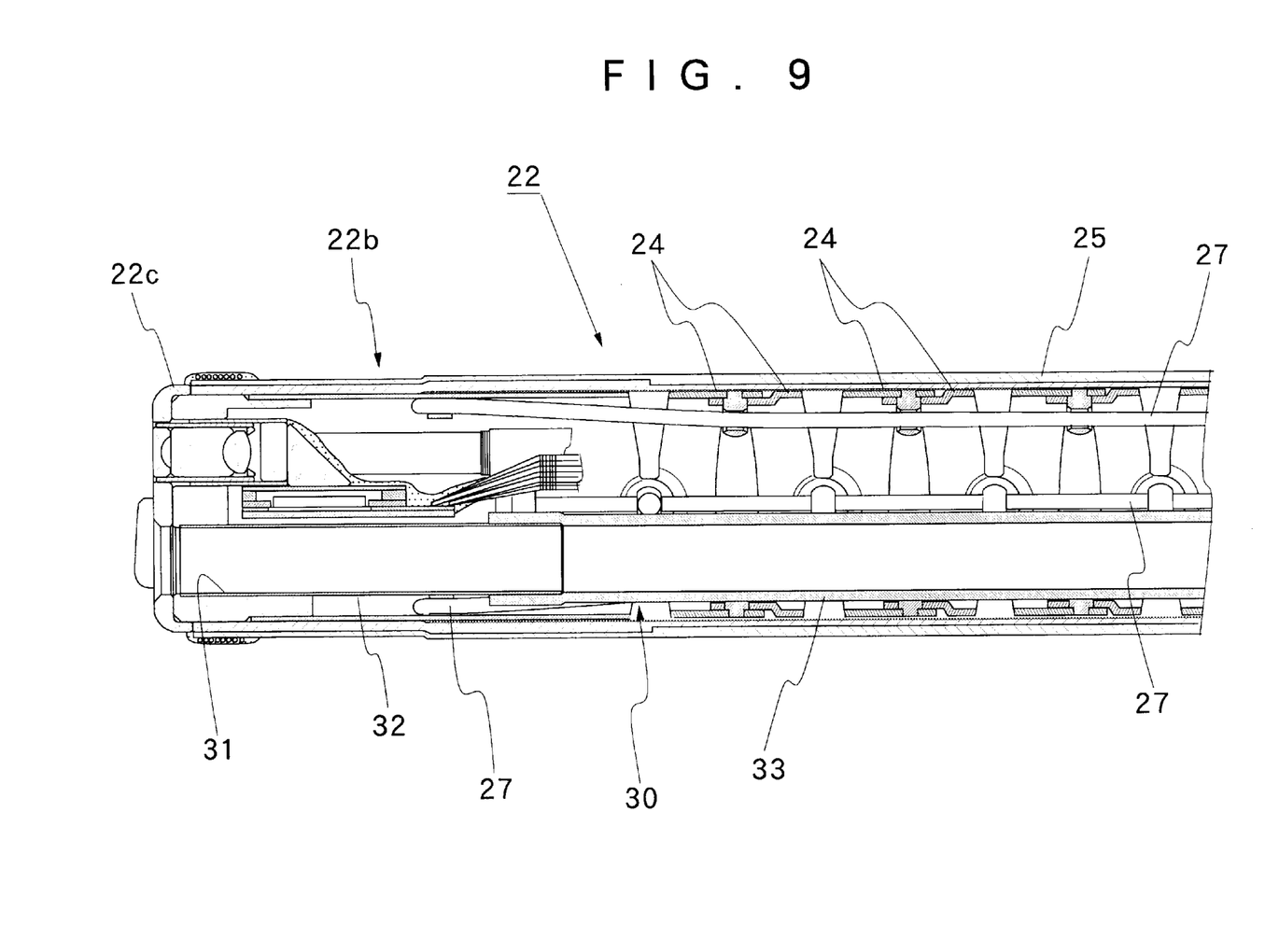
FIG. 9 is a schematic sectional view of a biopsy channel, shown as one of endoscopic component parts which are fitted and located internally of an angle section of the endoscopic insertion instrument.

Reference is now had to FIG. 8 which shows a general layout of an endoscope and to FIG. 9 which shows in section a fore end portion of an endoscopic insertion instrument. In these figures, indicated at 20 is an endoscope itself, including a manipulating head assembly 21, an insertion instrument 22 which is extended out on the front side of the manipulating head assembly 21 for introduction into a body cavity of a patient, and a universal cable 23 for disconnectibly connecting the endoscope to a light source and so forth.

The insertion instrument 22 is constituted by an elongated flexible body 22a, an angle section 22b and a rigid tip end section 22c successively from the side of the manipulating head assembly 21. Although not shown in the drawings, on a distal end face or on distal end portions, the rigid tip end section 22c is formed with an illumination window or windows for illuminating an intracavitary portion under observation, along with an observation window which is fitted with an image pickup means including an optical objective lens system and a solid-state image sensor device. The angle section 22b is provided for the purpose of turning the observation window on rigid tip end section 22c into arbitrary directions, and, as shown in FIG. 9, has a flexible bone structure which is constituted by a series of flexibly connected angle rings 24 and enshrouded in a flexible outer casing including an inner mesh layer and an outer skin layer. By manipulating an angle operating device 26, the angle section 22b can be angularly turned in upward, downward, rightward and leftward directions. For transmitting an operating force to the angle section 22b, a pair of upper and lower operating wires and a pair of right and left operating wires 27 are passed internally of the angle section 22b. One of the paired upper and lower operating wires 27 is pulled or loosened at the time of bending the angle section 22b in an upward or downward direction. On the other hand, one of the paired right and left operating wires 27 is pulled or loosened at the time of bending the angle section 22b in a rightward or leftward direction.

In FIG. 9, indicated at 30 is a biopsy channel which is provided coextensively in the endoscopic insertion instrument. The biopsy channel 30 is constituted by a through hole 31 which is provided on the rigid tip end section 22a, a connector pipe 32 which is partly fitted in the through hole 31, and a flexible tube 33 having a fore end portion thereof fitted on a proximal end portion of the connector pipe 32. The flexible tube 33 is constituted by a flexible tube which is same as the flexible tube 1 in construction and fabricated in the same manner as described hereinbefore. The fore open end of the above-mentioned through hole 31 on the rigid tip end section 22a provides an exit opening of the biopsy channel.

Figure 10:
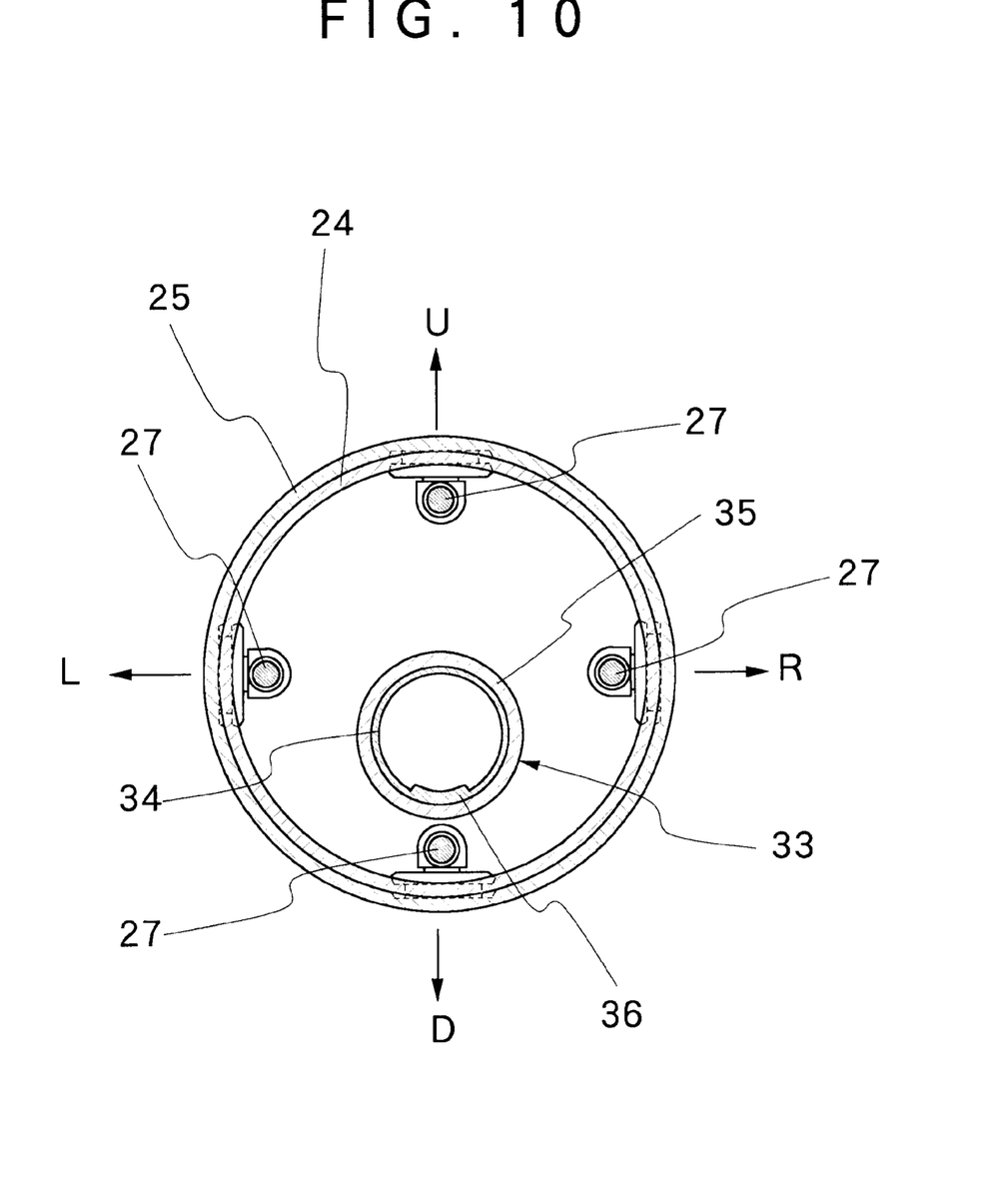
FIG. 10 is a transverse sectional view of the endoscopic insertion instrument, adopted for explanation of bending directions of the insertion instrument.

As seen in FIG. 10, the flexible tube 33 of the biopsy channel 30 is composed of an inner layer 34 and an outer layer 35 in the same manner as the above-described flexible tube 1. The inner layer 34 contains a thick wall portion 36 of a predetermined width B which extends longitudinally at one angular position around the circumference of the tubular inner layer 34. In the cross-sectional view of FIG. 10, the angle section 22b can be flexibly bent in upward, downward, leftward and rightward directions as indicated by arrows U, D, L and R, respectively. In this case, preferably the flexible tube 33 of the biopsy channel is fitted in the endoscopic insertion instrument such that the thick wall portion 36 of the inner layer 34 is positioned on the lower side, that is, on the side of the lower operating wire 27. Accordingly, when the angle section 22b is bent upward, the thick wall portion 36 of the inner layer 34 comes to lie along the outer side of an arcuate bend as shown particularly in FIG. 11.

Figure 11:
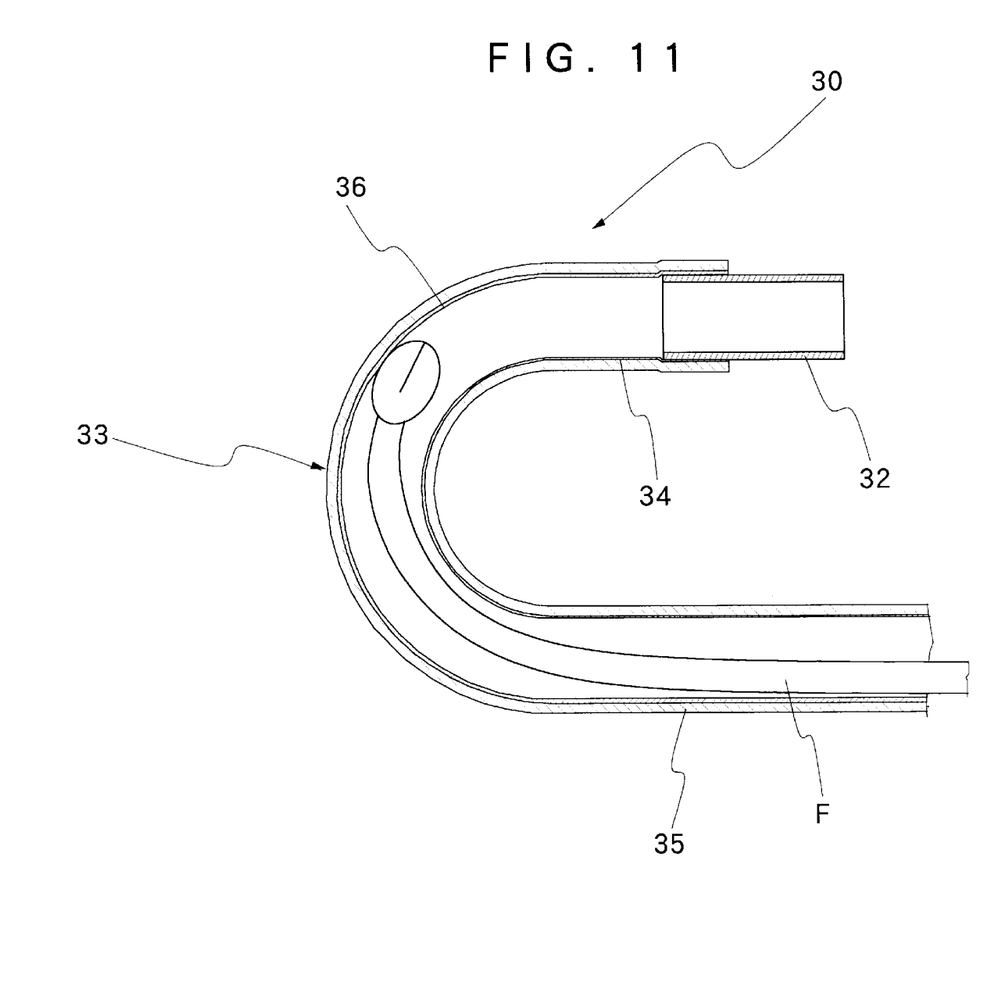
FIG. 11 is a schematic sectional view of the endoscopic insertion instrument which is bent into U-shape, and forceps being introduced into a biopsy channel of the endoscopic insertion instrument.

Therefore, for example, when a pair of forceps F are inserted into the biopsy channel 30 of the endoscopic insertion instrument which bent in the direction shown in FIG. 11, they are forcibly pressed and slid against inner surfaces of the biopsy channel 30 on the outer side of the bend as they are pushed forward toward the exit opening of the biopsy channel. In this regard, greater the angle of the bend in the endoscopic insertion instrument, the greater becomes the force which presses the forceps F against inner surfaces of the biopsy channel 30. However, even if forceps F or other instruments are repeatedly pressed and slid against the inner layer 34 of the biopsy channel 30 in this manner, there is little possibility of the inner layer being ruptured or damaged, because the thick wall portion 36 in the inner layer 34 of the flexible tube 33 of the biopsy channel 30 is located on the outer side of the bend as described above. In addition, the thick wall portion 36 in the inner layer 34 is extended parallel with the longitudinal axis of the flexible tube 33, it contains no stepped surface portions or such surface irregularities as would obstruct passage of forceps F or other inserted instruments.

On the other hand, except the thick wall portion 36, the inner layer 34 of the flexible tube 33 is constituted by a thin film of an almost infinitesimal thickness. Therefore, it becomes possible to reduce the diameter of the biopsy channel 30 or the diameter of the endoscopic insertion instrument 22. In other words, for the purpose of facilitating insertion of forceps F or other instruments, the inside diameter of the biopsy channel 30 can be increased without changing its outside diameter. Besides, the reduction in thickness of the inner layer 34 contributes to impart higher flexibility to the biopsy channel 30 as a whole particularly in bending directions.

Whenever forceps F or other instruments are inserted into the biopsy channel 30, they are inevitably brought into sliding contact with inner surfaces of the biopsy channel 30. The inner layer 34 of the biopsy channel 30 is extraordinarily small in thickness but has favorable slipperiness and low friction coefficient. Accordingly, unless the biopsy channel 30 is bent to an exceptionally acute angle as shown in FIG. 11, inserted forceps F or other biopsy or surgical instruments are allowed to advance smoothly within the biopsy channel 30 substantially free of resistive forces. In this respect, as long as inner surfaces of the biopsy channel 30 have sufficient properties in slipperiness and friction coefficient, normally it is immune from abrasive wear, frictional damages and so forth even if the inner layer 34 is in the form of a thin film of an infinitesimal thickness. However, in case the endoscopic insertion instrument is frequently used in an acutely bent form as shown in FIG. 11, inner surfaces of the biopsy channel 30 become more susceptible to abrasive wear and frictional damages.

When angularly bending the angle section 22b of the endoscopic insertion instrument within a body cavity to turn the rigid tip end section 22c into arbitrary directions, looking for a particular intracavitary site within a view field of the observation window on the rigid tip end section for a therapeutic treatment or for sampling tissues, it is usually the case that an operator tends to bend the angle section 22b in an upward direction most frequently and to a maximum degree. Accordingly, the location of the thick wall portion 36 on the outer side of an arcuate bend in the angle section 22b, which is turned in an upward direction, has great significance in the sense of reinforcement because the strength and durability of the biopsy channel 30 can be improved markedly.

Figure 12:
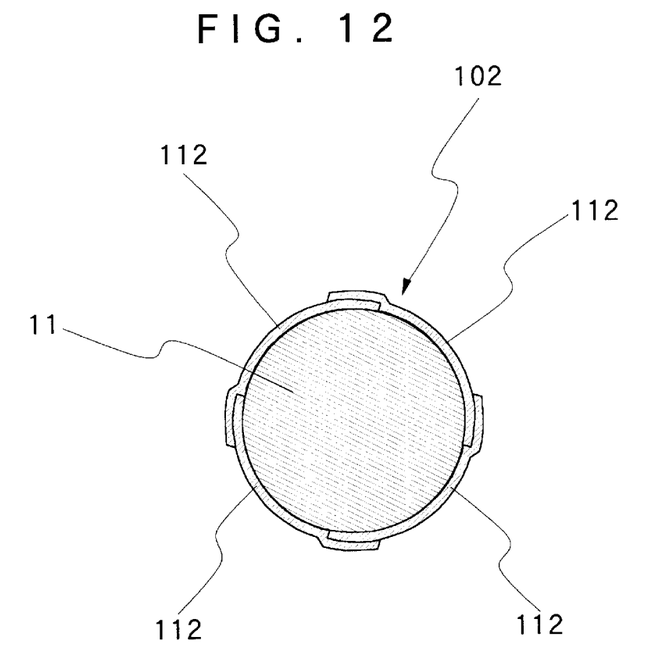
FIG. 12 is a schematic sectional view of an inner layer according to another embodiment of the invention.

Since the angle section which is flexibly bendable in upward, downward, rightward and leftward directions, it can be bent in any one of these directions when the forceps F is introduced into the biopsy channel 30. Therefore, the thick wall portion in the inner layer 34 can be provided in each one of these four directions (in a plural number of directions in which the angle section 22b is bent more frequently). In such a case, as shown in FIG. 12, a tubular inner layer 102 with four thick wall portions can be formed by overlapping lateral side portions of four thin film sheets 112 when forming same into a tube on a core rod 11.

In addition to endoscopic biopsy channels, the flexible tube according to the present invention can be applied as an air/water feed tube, an endoscopic guide tubes, a catheter, an outfit tube of a control cable for axially displacing an objective lens system of an endoscopic image pickup, or as a flexible stem portion of a biopsy or surgical instrument.

Figure 13:
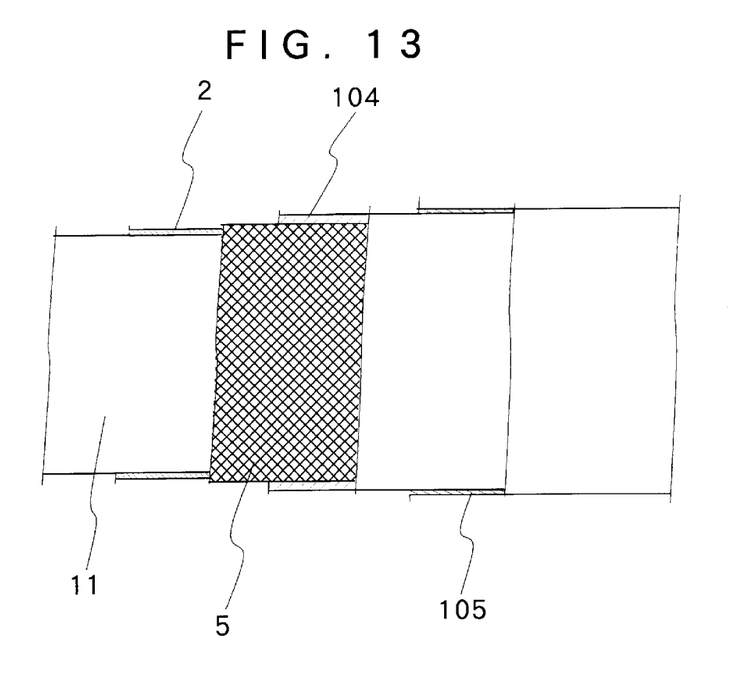
FIG. 13 is schematic partly cutaway view of a main tube body layer according to still another embodiment of the invention.

Further, in the above-described embodiment of the invention, the main tube body layer 4 is formed and laminated on and around the mesh layer 4 by extrusion molding. Alternatively, the main tube body layer 4 can also be formed in the manner as described below. Namely, for forming the main tube body layer, there may be employed a tube of a thermoplastic synthetic resin material, for example, an urethane resin tube 104 as shown in FIG. 13. Prior to fitting the urethane resin tube 104 on the mesh layer 5, the latter is knit around the inner layer 2 on a core rod 11 in the same manner as in the foregoing first embodiment. Then, the urethane resin tube 104 is fitted on the mesh layer 5. In so doing, the urethane resin tube 104 can be fitted on quite easily because its inside diameter is larger than the outside diameter of the mesh layer 5. Further, a heat-shrinkable tubing 105 is fitted on the urethane tube 104 which is fitted on the mesh layer 5 in the manner as described above.

Then, the tube assembly on the core rod 11, composed of four layers including the inner layer 2, mesh layer 5, urethane tube 104 and heat-shrinkable tube 105, is heated to integrate the respective layers. For this purpose, the heating temperature should lower than the firing temperature of the inner layer 2 but higher than a temperature at which the urethane tube 104 begins to soften. By a heating treatment, the urethane tube 104 which is interposed between the mesh layer 5 and the heat-shrinkable tube 105 heated to a softened or molten state. At the same time, the heat-shrinkable tube 105 on the outer side of the urethane tube 104 is shrunk into a smaller diameter, pressing the softened or molten urethane tube 104 into the mesh layer 5 to integrate these layers with each other.

Thereafter, after cooling, the heat-shrinkable tube 105 is removed by the use of a cutter or scissors to obtain the flexible tube 1 having the mesh layer 5 integrally and inseparably embedded in the main tube body layer 4 of the urethane tube 104. Thus, the flexible tube 1 is enhanced in strength and free of the problem of exfoliation or detachment of the main tube body layer 4 from the mesh layer 5 even if it is repeatedly bent to an acute angle or twisted from time to time.

What is claimed is:

1. A flexible tube, comprising:
    an outer layer including a main tube body layer formed of a thermoplastic synthetic resin in a predetermined thickness, and a reinforcing layer provided integrally on the inner side of said main tube body layer; and
    an inner layer formed of a thin film of air tight and low friction material provided on the inner side of said reinforcing layer;
    said inner layer being formed by rolling a thin film into a tubular form in such a way that opposite sides of said thin film are overlapped one on the other to a predetermined degree to form a thick wall portion of a predetermined width extending longitudinally of and at one angular position of said inner layer.

2. A flexible tube as defined in claim 1, wherein said inner layer is formed of a thin film substantially of uniform thickness rolled on itself by one turn until one lateral side of said thin film is overlapped on the other lateral side to a predetermined degree to formed a thick wall portion of a predetermined width extending longitudinally of and at one angular position of said inner layer.

3. A flexible tube as defined in claim 1, wherein said inner layer is formed of a thin film substantially of uniform thickness rolled on itself by a plural number turns.

4. A flexible tube fitted in an insertion instrument of an endoscope to serve as a biopsy channel for insertion of biopsy or surgical therapeutic instruments, said flexible tube comprising:

a laminated multi-layer structure including an outer layer including a main tube body layer formed of a thermoplastic synthetic resin in a predetermined thickness, and a reinforcing layer provided integrally on the inner side of said main tube body layer, and an inner layer formed of a thin film of air tight and low friction material provided on the inner side of said reinforcing layer;

said inner layer being formed by rolling a thin film into a tubular form in such a way that opposite sides of said thin film are overlapped one on the other over a predetermined width to form a thick wall portion of a predetermined width extending in the longitudinal direction of said inner layer; and said thick wall portion being located in an angular position of said biopsy channel where said biopsy or surgical instrument are slid against an inner surface of said biopsy channel when an angle section of said endoscopic instrument is flexibly bent into an angular form.

5. A flexible tube as defined in claim 4, wherein said angle section is flexibly bendable at least in two predetermined directions, and said inner layer is formed of a plural number of thin films to provide longitudinal thick wall portions of a predetermined width at such two separate angular positions of said inner layer that each thick wall portion is located on the outer side of a bend when said angle section of said endoscopic insertion instrument is bent in either one of said two directions.

6. A flexible tube as defined in claim 4, wherein said inner layer is formed of a thin film of either non-calcined tetrafluoroethylene resin or non-calcined hexafluoroethylene resin.

7. A flexible tube as defined in claim 1 or 4, wherein said main tube body layer is formed of at least one member selected from a group consisting of urethane resin, nylon and polyethylene, and said reinforcing layer is formed of metal netting in the form of knit fabric of metallic filaments.

8. A method for manufacturing a flexible tube having a laminated multi-layer structure including an outer layer including a main tube body layer formed of a thermoplastic synthetic resin in a predetermined thickness, and a reinforcing layer provided integrally on the inner side of said main tube body layer, and an inner layer formed of a thin film of air tight and low friction material provided on the inner side of said reinforcing layer, said method comprising the steps of:

forming said inner layer by wrapping an elongated strip of a thin film sheet around a core rod in such a way that opposite lateral sides of said thin film sheet are overlapped one on the other to a predetermined degree to provide a thick wall portion of a predetermined width extending longitudinally of and at one angular position of said inner layer;

etching outer peripheral surfaces of said inner layer on said core rod;

forming a reinforcing mesh layer on and around said inner layer by knitting metal filaments directly on and around etched outer surfaces of said inner layer; and forming said main tube body layer by laminating a thermoplastic resin on and around said reinforcing mesh layer.

* * * * *